(12) United States Patent
Li

(10) Patent No.: US 10,112,664 B2
(45) Date of Patent: Oct. 30, 2018

(54) CLIMBING ROBOT VEHICLE

(71) Applicant: ZHEJIANG UNIVERSITY, Hangzhou (CN)

(72) Inventor: Xin Li, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/650,312

(22) Filed: Jul. 14, 2017

(65) Prior Publication Data
US 2017/0313369 A1 Nov. 2, 2017

Related U.S. Application Data

(63) Continuation of application No. 14/906,451, filed on Jan. 20, 2016, now Pat. No. 9,738,337.

(30) Foreign Application Priority Data

Jan. 29, 2014 (CN) .......................... 2014 1 0042713

(51) Int. Cl.
B62D 57/024 (2006.01)
B62D 57/04 (2006.01)
(Continued)

(52) U.S. Cl.
CPC ............ B62D 57/024 (2013.01); B25J 15/06 (2013.01); B62D 57/04 (2013.01); G01N 29/225 (2013.01); G01N 29/265 (2013.01)

(58) Field of Classification Search
CPC ...... B62D 57/00; B62D 57/024; B62D 57/04; B25J 15/06; A47L 11/38; A47L 1/02; A47L 2201/00
See application file for complete search history.

(56) References Cited

U.S. PATENT DOCUMENTS 4,095,378 A * 6/1978 Urakami ................. B24C 3/062
 114/222
4,688,289 A * 8/1987 Urakami ................... B08B 1/04
 114/222
(Continued)

Primary Examiner — Joseph M Rocca
Assistant Examiner — Michael R Stabley
(74) Attorney, Agent, or Firm — Platinum Intellectual Property LLP

(57) ABSTRACT

A climbing robot vehicle comprises a vehicle (2) and the front and rear ends of the vehicle body are provided with wheels (3). The end of the vehicle body facing towards the wall is fixedly connected to a sucking mechanism. The sucking mechanism comprises a body, the body being a hollow cylinder (4). A cover plate (5) is provided above the hollow cylinder. The upper end face of the cover plate is fixedly connected with the vehicle body and the lower end face of the cover plate is fixedly connected with the outer edge of the upper end face of the hollow cylinder by means of the first blocks (43) spaced from each other. The inner wall of the hollow cylinder is provided with tangential nozzles (41). The space between the first blocks (43) forms a first exhaust duct (44) between the outer edge of the upper end face of the hollow cylinder and the lower end face of the cover. A gap is formed between the lower end face of the hollow cylinder and the wall, and the gap forms a second exhaust duct (42) between the outer edge of the lower end face of the hollow cylinder and the wall. The climbing robot vehicle can be sucked on various kinds of walls and has a strong sucking ability and a wide application range.

11 Claims, 10 Drawing Sheets

(51) Int. Cl.
*B25J 15/06* (2006.01)
*G01N 29/22* (2006.01)
*G01N 29/265* (2006.01)

(56) References Cited

U.S. PATENT DOCUMENTS

| | | | | |
|---|---|---|---|---|
| 4,809,383 | A * | 3/1989 | Urakami | B08B 1/04 |
| | | | | 114/222 |
| 4,860,400 | A * | 8/1989 | Urakami | B08B 1/04 |
| | | | | 114/222 |
| 4,926,957 | A * | 5/1990 | Urakami | B62D 57/024 |
| | | | | 114/222 |
| 5,014,803 | A * | 5/1991 | Urakami | B62D 57/024 |
| | | | | 114/222 |
| 5,592,998 | A * | 1/1997 | Urakami | B62D 57/00 |
| | | | | 180/164 |
| 5,752,577 | A * | 5/1998 | Urakami | B62D 57/00 |
| | | | | 180/164 |
| 6,353,963 | B1 * | 3/2002 | Bair | A47L 5/28 |
| | | | | 15/351 |
| 6,913,524 | B2 * | 7/2005 | Urakami | B62D 57/02 |
| | | | | 269/21 |
| 7,520,356 | B2 * | 4/2009 | Sadegh | B62D 49/0621 |
| | | | | 180/127 |
| 7,753,755 | B2 * | 7/2010 | Clark, Jr. | A63H 17/26 |
| | | | | 446/117 |
| 7,980,916 | B2 * | 7/2011 | Clark, Jr. | A63H 17/26 |
| | | | | 446/177 |
| 8,240,000 | B2 * | 8/2012 | Oh | A47L 5/30 |
| | | | | 15/347 |

\* cited by examiner

CLIMBING ROBOT VEHICLE

BACKGROUND OF THE INVENTION

The invention is related to a climbing robot vehicle.

A climbing robot vehicle is able to walk on the vertical walls and ceilings, and in many specific occasions plays an important role. For example, we install ultrasonic flaw detector on the vehicle, then the climbing robot vehicle can replace people to carry out flaw detection of large-scale buildings (bridges, tunnels, etc.), greatly reducing the operation cost and shortening the working hours.

In order to make the climbing robot vehicle clinging to the wall, we need to apply a pressure pointing to the wall on the vehicle. When the climbing robot vehicle clings to a vertical wall, the pressure generates a friction force between the vehicle and the wall. The friction force not only overcomes the gravity of the vehicle itself, but also provides a driving force required for moving the vehicle; when the climbing robot vehicle clings to the ceiling wall, a part of the pressure directly overcomes the gravity of the vehicle itself, and the residual pressure generates a friction force between the vehicle and the wall, providing a driving force for the movement of the vehicle.

The invention whose patent application number is CN201210405689 discloses a climbing robot vehicle, and the robot is equipped with an electromagnetic sucker which generates a suction force. However, the drawback is that the wall the robot climbs must have a magnetic field in order to generate a suction force, which greatly limits its application.

SUMMARY OF THE INVENTION

In order to overcome the application limitations of the existing climbing robot vehicles, the invention provides a climbing robot vehicle.

The technical proposal of the invention is that:

A climbing robot vehicle comprises a vehicle, and the front and rear ends of the vehicle are provided with wheels. The end of the vehicle facing towards the wall is fixedly connected to a sucking mechanism. The sucking mechanism comprises a body, wherein the body is a hollow cylinder. A cover plate is provided above the hollow cylinder. The upper end face of the cover plate is fixedly connected with the vehicle and the lower end face of the cover plate is fixedly connected with the outer edge of the upper end face of the hollow cylinder by means of the first blocks spaced from each other. The inner wall of the hollow cylinder is provided with a tangential nozzle. The space between the first blocks forms a first exhaust duct between the outer edge of the upper end face of the hollow cylinder and the lower end face of the cover plate. A gap is formed between the lower end face of the hollow cylinder and the wall, and the gap forms a second exhaust duct between the out edge of the lower end face of the hollow cylinder and the wall. The first exhaust duct and the second exhaust duct connect the interior of the hollow cylinder with the outer peripheral environment respectively.

Further, the upper end face of the vehicle is provided with an electric motor which is connected to the cover plate by means of its driving screw; the screw is connected to the screw thread of the cover plate; the hollow cylinder and the cover plate are provided with pressure measuring holes, the pressure measuring holes are connected with pressure sensors.

Further, the vehicle is connected with the hollow cylinder by means of connecting rods, which are provided on the outer edge of the upper end face of the hollow cylinder; both ends of the connecting rods are processed with a screw; the intermediate section of the connecting rod is a cylinder, and stairs are provided between the cylinder and the screw. The screws on the two ends are fixedly connected with the screw thread of the vehicle and that of the hollow cylinder respectively. The position of the cover plate corresponding to the connecting rod is provided with a through hole which is slidably matched with the cylinder located in the intermediate section of the connecting rods. The space between the cover plate and the hollow cylinder forms a first exhaust duct.

Further, the vehicle is provided with guide holes; the inside of the each of guide holes is provided with a guide column. One end of the guide column is fixedly connected to the upper end face of the cover plate through the guide hole. The guide columns can slide in the guide holes.

Further, the outer edge of the lower end face of the hollow cylinder is provided with a soft pad.

Further, the soft pad is a bristle strip.

Further, the lower part of the hollow cylinder is provided with an annular baffle, the upper end surface of the annular baffle is fixedly connected with the outer edge of the lower end face of the hollow cylinder by means of the second blocks; the second blocks cover part of the area of the annular baffle. The space between the second blocks forms a third exhaust duct between the outer edge of the lower end face of the hollow cylinder and the annular baffle. The third exhaust duct connects the interior of the hollow cylinder and the outer peripheral environment; The lower end face of the annular baffle is provided with a soft pad.

Further, the first blocks are equally spaced between the lower end face of said cover plate and the outer edge of the upper end face of the hollow cylinder, and the second blocks are equally spaced between the upper end face of said annular baffle and the lower end face of said hollow cylinder.

Further, the tangential nozzles are connected with a high pressure fluid source by means of pipes. The high pressure fluid source includes high pressure liquid source and high pressure gas source. The high pressure gas source may be an air compressor, a fuel engine or a turbojet engine and so on; the high pressure liquid source may be a high pressure pump.

The advantages of the present invention are embodied in that:

1. The first exhaust duct is provided to eliminate the local high pressure distribution which the lower surface of the cover plate forms, thereby ensuring that a pressure is applied to the vehicle. When the climbing robot vehicle clings to a vertical wall, the pressure generates a friction force between the vehicle and the wall. The friction force not only overcomes the gravity of the vehicle itself, but also provides a driving force required for moving the vehicle.

2. The second exhaust duct is provided to avoid contact between the lower end face of the hollow cylinder and the wall, so the vehicle can travel smoothly on the wall.

3. By adjusting the height of the first exhaust duct between the hollow cylinder and the cover plate, and the height of the second exhaust duct between the hollow cylinder and the wall, the pressure which the vehicle bears is always at or near the maximum value.

4. A soft pad is provided to block the exhaust flow of the second exhaust duct between the wall and the hollow cylinder, thus eliminating the disturbance flow caused by concavity, convexity and unevenness of the wall in the second exhaust duct, maximally inhibited the impact which concave, convex and unevenness of the wall have on the pressure distribution; the soft pad also blocks the air entering the airflow in the hollow cylinder from the outside reflux, maximally protecting the rotation flow in the hollow cylinder.

5. The third exhaust duct is provided to reduce the pressure on the part between the annular baffle and the wall and beyond the soft pad, thereby increasing the pressure which the robot vehicle bears.

DETAILED DESCRIPTION OF THE INVENTION

Herebelow, embodiment of the present invention will be described in detail with reference to the drawings.

Embodiment 1

Figure 1A:
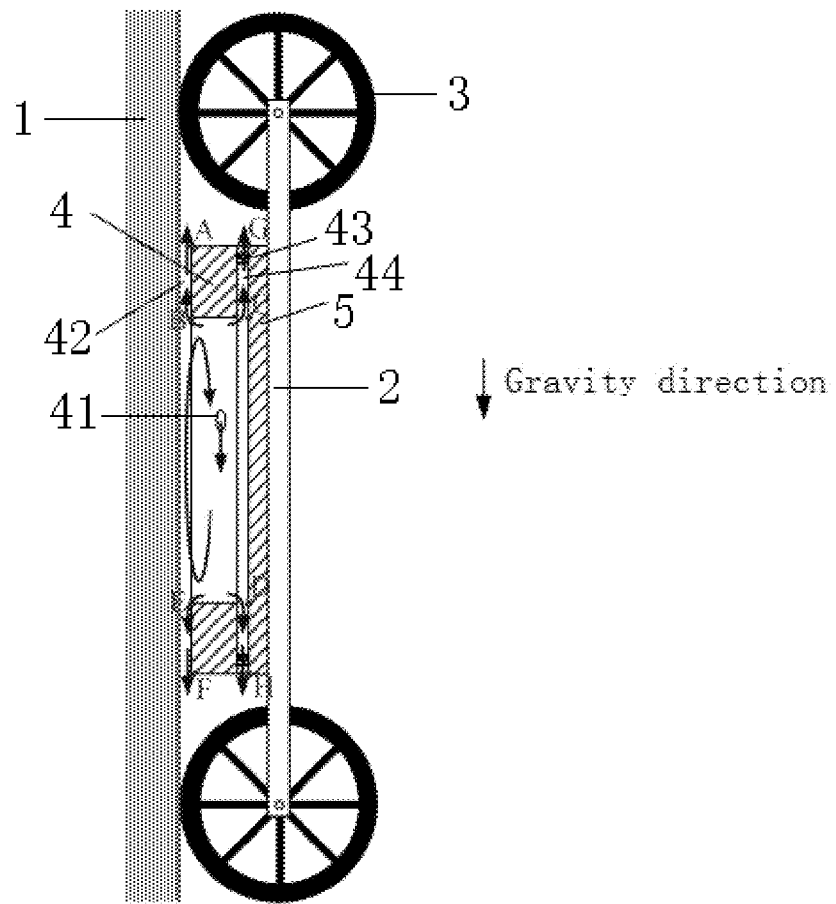
FIG. 1a represents a schematic diagram of the embodiment 1 of the invention.
Figure 1B:
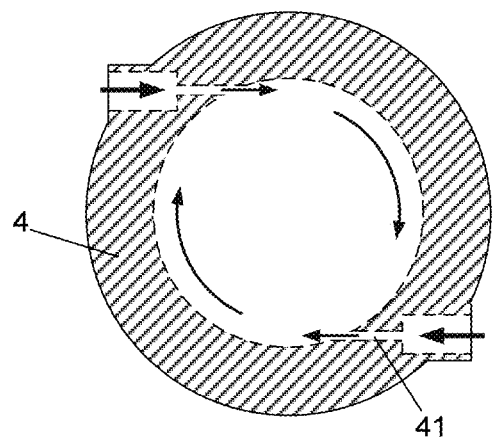
FIG. 1b represents a sectional view of the hollow cylinder at the position of the tangential nozzle.
Figure 1C:
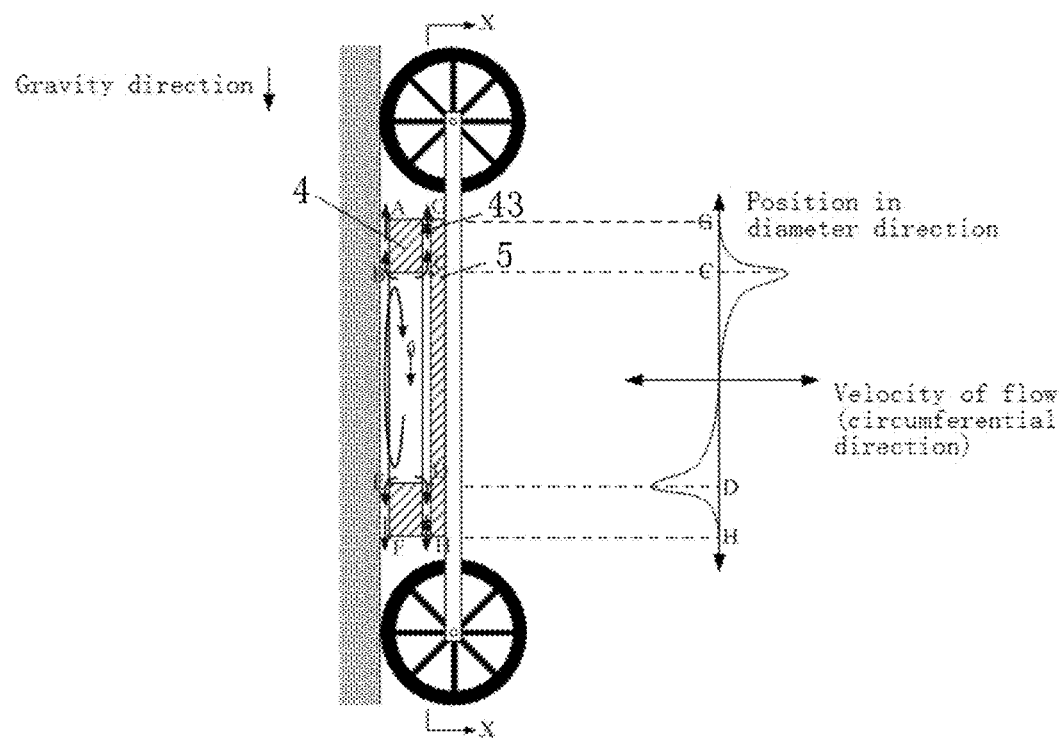
FIG. 1c represents a distribution view of the velocity component of the airflow in the circumferential direction of the C-G surface and the D-H surface in the embodiment 1.

Climbing robot vehicle according to FIG. 1a, FIG. 1b and FIG. 1c, comprises a vehicle 2 and the front and rear ends of the vehicle 2 are provided with wheels 3. The end of the vehicle 2 facing towards the wall 1 is fixedly connected with a sucking mechanism. The sucking mechanism comprises a body, wherein the body being a hollow cylinder 4. A cover plate 5 is provided above the hollow cylinder 4. The inner wall of the hollow cylinder 4 is provided with tangential nozzles 41. The upper end face of the cover plate 5 is fixedly connected with the vehicle 2 and the lower end face of the cover plate 5 is fixedly connected with the outer edge of the upper end face of the hollow cylinder 4 by means of the first blocks 43 spaced from each other. The space between the first blocks 43 forms a first exhaust duct 44 between the outer edge of the upper end face of the hollow cylinder and the lower end face of the cover plate. A gap is formed between the lower end face of the hollow cylinder 4 and the wall, and the gap forms a second exhaust duct 42 between the out edge of the lower end face of the hollow cylinder and the wall. The first exhaust duct 44 and the second exhaust duct 42 connected the interior of the hollow cylinder with the outer peripheral environment respectively.

After the upstream of the tangential nozzles supply pressurized air, the air is ejected from the nozzles at high speed and rotating along the circular wall of the hollow cylinder. After rotating, a part of the air is discharged through the first exhaust duct, and the other part is discharged through the second exhaust duct. The first exhaust duct and the second exhaust duct both play very important roles. The following description details the role of the two exhaust ducts.

In order to facilitate the following description, some of the key points of the vehicle are marked (see FIG. 1a). Pressure which the vehicle bears is the sum of the pressure distribution generated by that airflow (if not specified, the pressure here refers to gauge pressure) in the A-B, C-D and E-F surface.

Figure 2:
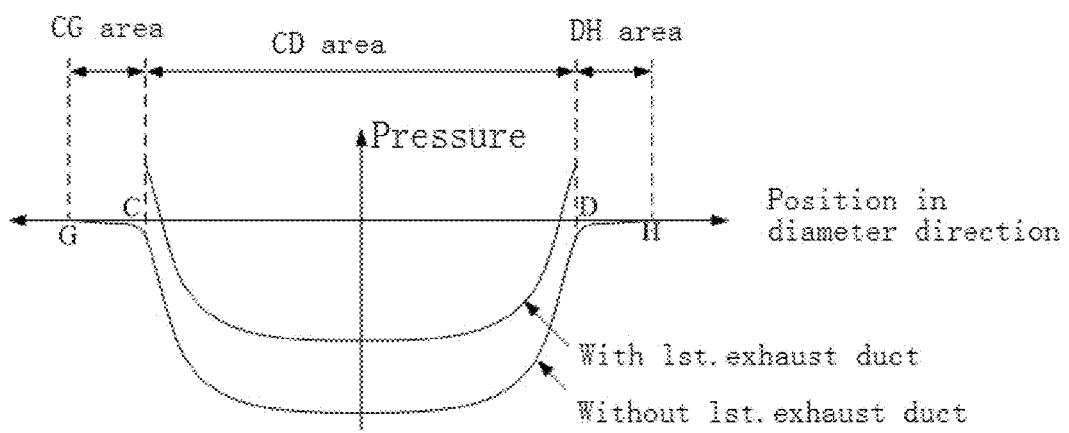
FIG. 2 represents a comparison view of pressure distribution between the embodiment of not setting the first exhaust duct and embodiment of setting the first exhaust duct.
Figure 3:
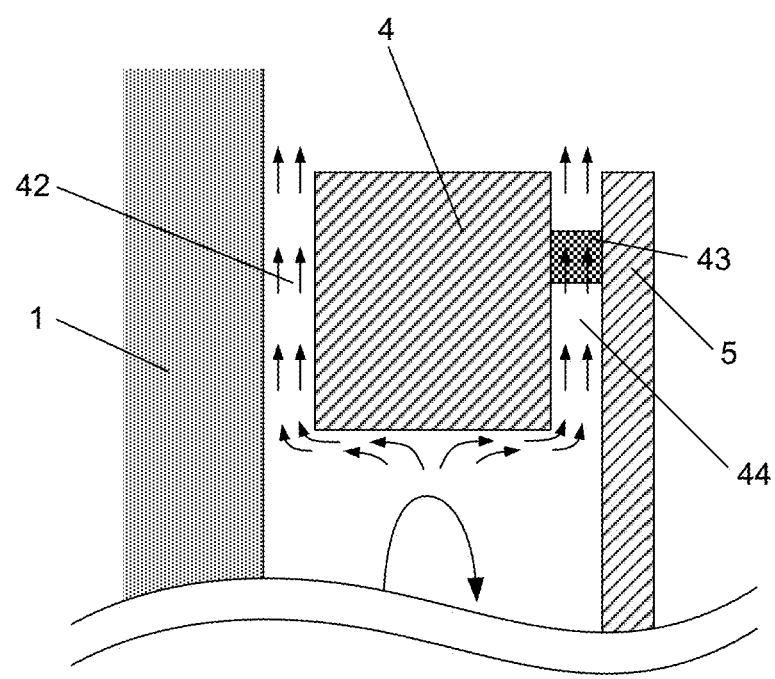
FIG. 3 represents a schematic diagram of the flow of dense air near the inner wall of the hollow cylinder after provided with the first exhaust duct.

The role of the first exhaust duct:

The first exhaust duct mainly affects the pressure distribution of C-D surface. Air rotates in the hollow cylinder, then the air of the central part of the hollow cylinder will be thrown to the outer periphery by a centrifugal force, which makes the air of the central part become thin, while the air near the inner wall of the hollow cylinder becomes dense, i.e., the pressure distribution will be in a concave shape in the hollow cylinder, where the center pressure is low and the outer pressure is high (as shown in FIG. 2). If there is no first exhaust duct, peripheral pressure distribution of the C-D surface will be high, i.e., the gauge pressure will be greater than zero. This high pressure part not only exerts a repulsive force on the vehicle, but also makes the concave-shaped pressure distribution in the hollow cylinder move in the direction of the high pressure. These will weaken the pressure which the vehicle bears. The first exhaust duct between the upper end face of the hollow cylinder and the cover plate can greatly improve the pressure. The first exhaust duct connects the inner of the hollow cylinder with outer environment, and the air which is thrown by the centrifugal force of the rotating airflow into the outer circumferential surface will flow into and through the first exhaust duct, channeling the dense air near the inner wall of the hollow cylinder, forming the flow as shown in FIG. 3, thereby reducing the high pressure near the inner wall of the hollow cylinder. Also, because the first exhaust duct is located in the same cross section with the C-D surface and therefore the C-D surface is the most downstream of the flow, pressure of the C-D surface is lower than other cross sections. In addition, the airflow has a tangential velocity component when entering the first exhaust duct. As the air flows through the first exhaust duct, the flow velocity component is gradually reduced to zero under the effect of viscous friction. FIG. 1c represents a distribution view of the tangential component of the velocity of the airflow in the first exhaust duct (i.e., the C-G and D-H segments). By analyzing the equation of fluid motion (i.e., the Navier-Stokes equation), the tangential velocity component can affect the pressure distribution in the radial direction. When the first exhaust duct is at an appropriate height, the velocity component of the circumferential direction will form a weak low pressure distribution in the first exhaust duct. Because the first exhaust duct is located in the same cross section with the C-D surface, the low pressure distribution formed in the first exhaust duct can cause the pressure distribution of the C-D surface to move in the direction of the low pressure, as shown in FIG. 2. In summary, the first exhaust duct can improve the pressure which the vehicle bears.

The role of the second exhaust duct:

The second exhaust duct is provided to avoid contact between the lower end face of the hollow cylinder and the wall, so the vehicle can travel smoothly on the wall. If there is no second exhaust duct, then friction will be formed between the lower end face of the hollow cylinder and the wall, hindering the vehicle travelling on the wall; if there are obstacles such as a convexity on the wall, collision will happen between the hollow cylinder and the obstacles, making the vehicle stuck. Another role of the second exhaust duct is to make the A-B surface and E-F surface produce a weak low pressure distribution. A part of the airflow has a velocity component in the direction of the circumference when entering the second exhaust duct. As the air flows through the second exhaust duct, the flow velocity component is gradually reduced to zero under the effect of viscous friction. By analyzing the equation of fluid motion (i.e., the Navier-Stokes equation), the velocity component of the circumferential direction can affect the pressure distribution in the radial direction. When the second exhaust duct is at an appropriate height, the velocity component of the circumferential direction will form a weak low pressure distribution in the second exhaust duct (i.e., the A-B and E-F segments). The low pressure distribution can exert a pressure on the vehicle, thereby increasing the total pressure which the vehicle bears.

Embodiment 2

Figure 4:
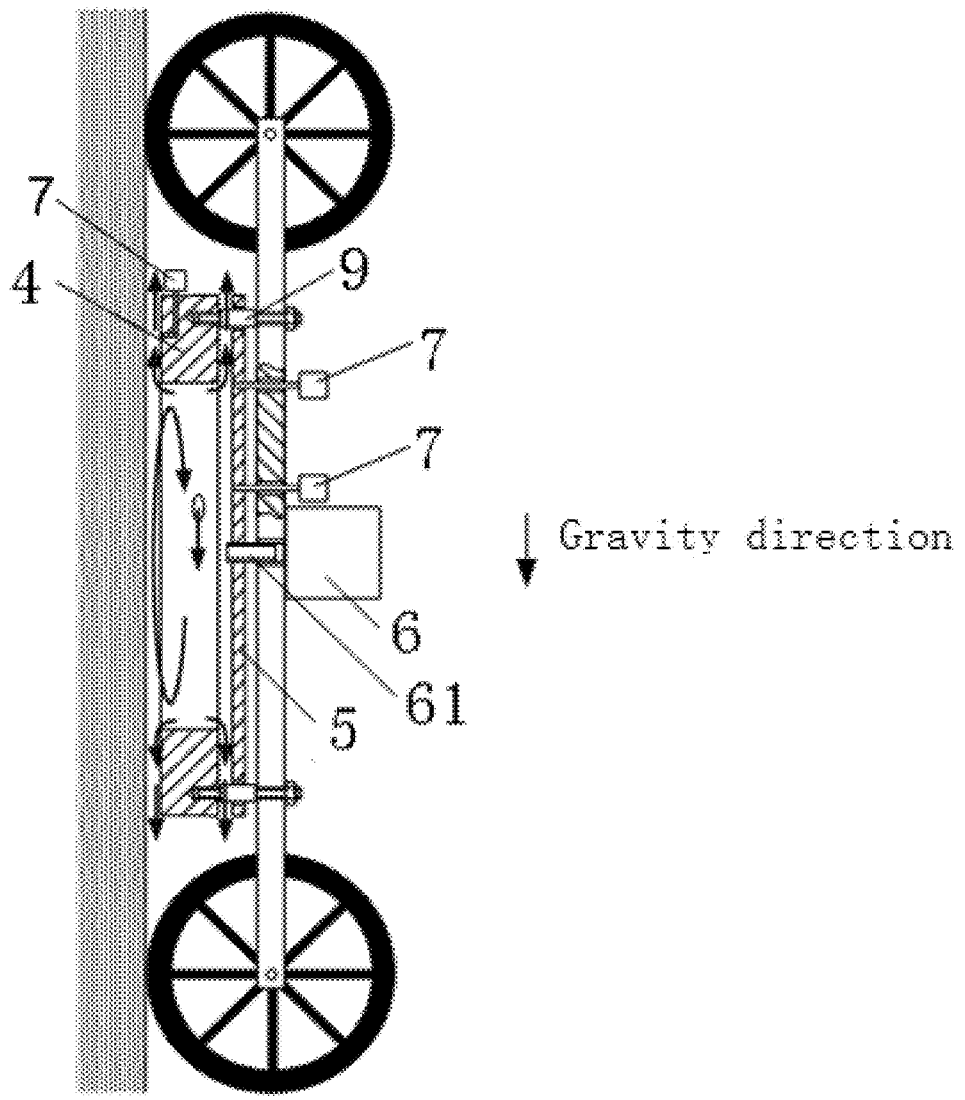
FIG. 4 represents a schematic diagram of the embodiment 2 of the invention.

According to FIG. 4, on the basis of the above embodiment 1, the upper end face of the vehicle 2 is provided with an electric motor 6, while the electric motor 6 is connected with the cover plate 5 by means of the screw 61 it drives; the screw 61 is connected with the screw thread of the cover plate 5; the cover plate 5 is provided with pressure measuring holes which are connected with pressure sensors 7; the cover plate is connected with the hollow cylinder 4 by means of connecting rods 9, while the connecting rods 9 are provided on the outer edge of the upper end face of the hollow cylinder 4; both ends of the connecting rods 9 are processed with a screw, the intermediate section of the connecting rod is a cylinder, and stairs are provided between the cylinder and the screw. Both ends of the screw are fixedly connected with the screw thread of the vehicle and that of the hollow cylinder respectively. The position in the cover plate corresponding to the connecting rod is provided with a through hole, and the through hole is slidably matched with the cylinder located in the intermediate section of the connecting rod. The space between the cover plate and the hollow cylinder forms a first exhaust duct.

In this embodiment, after rotating in the hollow cylinder, a part of the air is discharged through the first exhaust duct, and the other part is discharged through the second exhaust duct. This embodiment is a further improvement scheme of the embodiment 1, which can automatically adjust the height of the first exhaust duct.

In this embodiment, the hollow cylinder is connected with the vehicle by means of a plurality of connecting rods. Both ends of the connecting rod is processed with a screw, the intermediate section of the connecting rod is a cylinder, and stairs are provided between the cylindrical and the screw. The position of the cover plate corresponding to the connecting rod is provided with a through hole, the through hole is slidably matched with the cylinder located in the intermediate section of the connecting rod. Therefore, the cover plate is limited by the connecting rod so that it will not tilt when moving. The hollow cylinder and the cover plate is provided with one or a plurality of pressure measuring holes, while the pressure measuring holes are connected with pressure sensors. The electric motor will adjust the height of the first exhaust duct according to pressure signals measured by the pressure sensors. The purpose is to make the pressure which the vehicle bears always at or near the maximum value. The necessity of this design is illustrated in the following example.

Consider the case that the wheels of the vehicle have a leakage. When leakage occurs, the radius of the wheels will be smaller, which leads to the reduction of the space between the vehicle and the wall, and thus the height of the second exhaust duct which is formed between the hollow cylinder and the wall. This will lead to an increase of the viscosity friction of the air flow through the second exhaust duct. Then, the pressure distribution of the second exhaust duct (i.e., the A-B and E-F surface) will move in the direction of the high pressure. In addition, because the viscous friction of the second exhaust duct increases, part of the air will instead go to the first exhaust duct between the cover plate and the hollow cylinder. More airflow through the first exhaust duct will lead to the pressure distribution of the first exhaust duct (that is, the C-G and D-H surface) moving towards the direction of the high pressure, and thus lead to the pressure distribution of the C-D surface moving towards the direction of high pressure. The above-mentioned factors will weaken the pressure which the vehicle bears. In order to solve this problem, the implementation scheme is adopted to adjust the height of the first exhaust duct. We use the pressure sensors to detect the pressure changes in the hollow cylinder and the exhaust duct in real-time, and adjust the height of the first exhaust duct according to the pressure change.

Three pressure sensors are used to detect the pressure of three positions respectively as shown in FIG. 4, wherein one of the three pressure sensors is connected by means of a pressure measuring hole in the middle of the first exhaust duct, which can reflect the pressure change in the first exhaust duct; one is connected by means of a pressure measuring hole near the center of the hollow cylinder, which can reflect the pressure change in the hollow cylinder; one is arranged on the hollow cylinder, measuring the pressure change of the second exhaust duct by a pressure measuring hole. In case of leakage of the wheels, three pressure sensors will detect the increase of pressure. At this point, we need to increase the height of the first exhaust duct, so that the viscous friction decreases when the air flows through the first exhaust duct, thereby reducing the pressure distribution in the first exhaust duct. In addition, after the height of the first exhaust port increases, more air flows through the first exhaust duct, thereby reducing the airflow through the second exhaust duct, and therefore reducing the pressure in the second exhaust duct. To sum up, we can increase the height of the first exhaust duct until the detected values of the three pressure sensors drop to the lowest value, ensuring that the pressure which the vehicle bears is at or near the maximum value.

Embodiment 3

Figure 5:
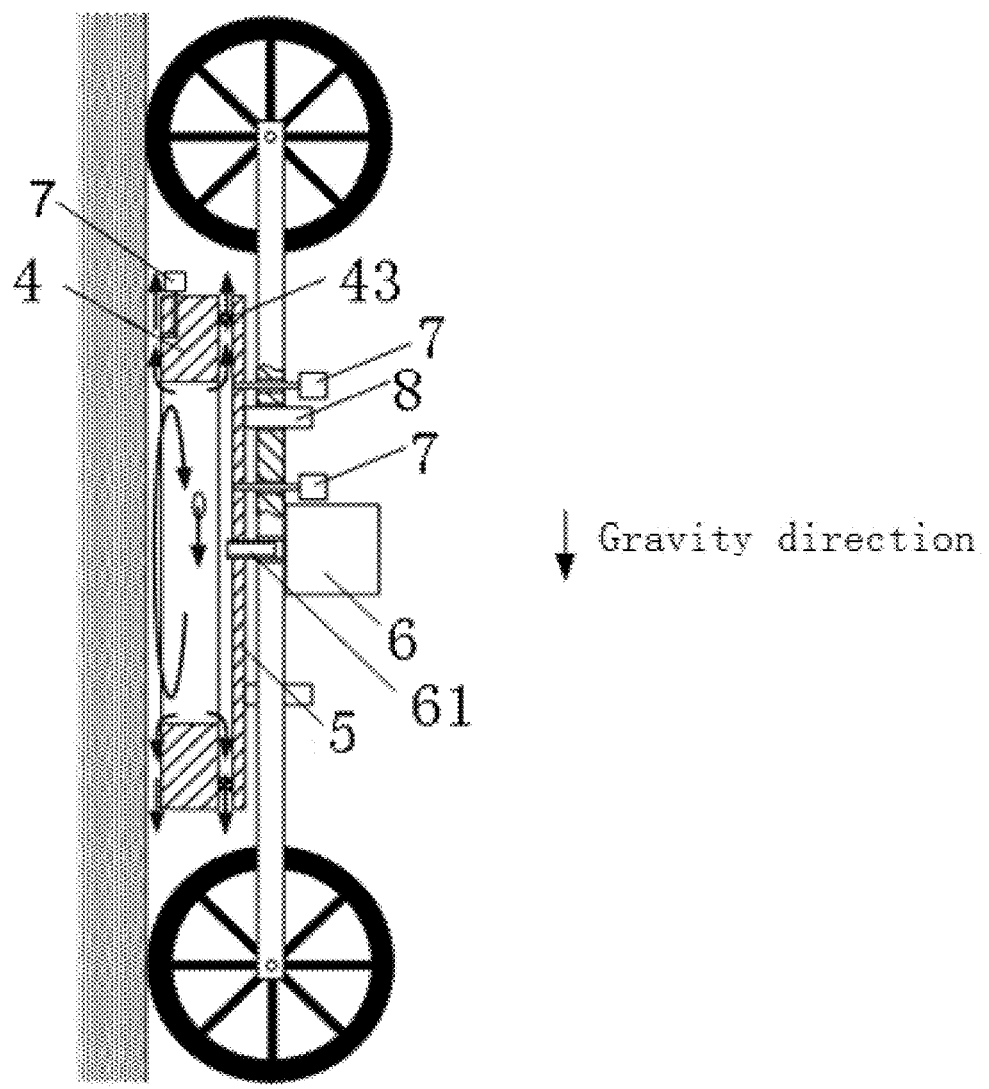
FIG. 5 represents a schematic diagram of the embodiment 3 of the invention.

According to FIG. 5, on the basis of the above embodiment 1, the upper end face of the vehicle 2 is provided with an electric motor 6, while the electric motor 6 is connected with the cover plate 5 by means of the screw 61 it drives; the screw 61 is connected with the screw thread of the cover plate 5; the cover plate 5 and the hollow cylinder 4 are provided with pressure measuring holes, and the pressure measuring holes are connected with pressure sensors 7. The vehicle 2 is provided with guide holes. The inside of each of guide hole is provided with a guide column 8. One end of the guide column 8 is fixedly connected to the upper end face of the cover plate 5 through the guide hole. The guide column 8 can slide in the guide hole.

In this embodiment, after rotating in the hollow cylinder, a part of the air is discharged through the first exhaust duct, and the other part is discharged through the second exhaust duct. This embodiment is a further improvement scheme of the embodiment 1, which can automatically adjust the height of the second exhaust duct. The cover plate is fixedly connected with the hollow cylinder with pads. An electric motor is fixed on the vehicle, the motor shaft is processed with a screw, and the center of the cover plate is processed with a matching screw hole. The electric motor drives the cover plate and the hollow cylinder to move with the screw. The guide column is fixedly installed on the upper surface of the cover plate. The guide column extends into the guide hole processed on the vehicle and slides in the guide hole. The hollow cylinder is limited by the guide column and guide hole so that it will not tilt when moving. The hollow cylinder and the cover plate is provided with one or a plurality of pressure measuring holes, the pressure measuring holes are connected with pressure sensors. The electric motor will adjust the height of the first exhaust duct according to pressure signals measured by the pressure sensors. The purpose is to make the pressure which the vehicle bears always at or near the maximum value. The necessity of this design is illustrated in the following example.

Consider the case that the wheels of the vehicle have a leakage. When leakage occurs, the radius of the wheels will be smaller, which leads to the reduction of the space between the vehicle and the wall, and thus the height of the second exhaust duct which is formed between the hollow cylinder and the wall. This will lead to an increase of the viscosity friction of the air flow through the second exhaust duct. Then, the pressure distribution of the second exhaust duct (i.e., the A-B and E-F surface) will move in the direction of high pressure. In addition, because the viscous friction of the second exhaust duct increases, part of the air will instead go to the first exhaust duct between the cover plate and the hollow cylinder. More airflow through the first exhaust duct will lead to the pressure distribution of the first exhaust duct (that is, the C-G and D-H surface) moving towards the direction of the high pressure, and thus lead to the pressure distribution of the C-D surface moving towards the direction of high pressure. The above-mentioned factors will weaken the pressure which the vehicle bears. In order to solve this problem, the implementation scheme is adopted to adjust the height of the second exhaust duct. We use the pressure sensors to detect the pressure changes in the hollow cylinder and the exhaust duct in real-time, and adjust the height of the second exhaust duct according to the pressure change.

Three pressure sensors are used to detect the pressure of three positions respectively as shown in FIG. 5, wherein one of the three pressure sensors is connected by means of a pressure measuring hole in the middle of the first exhaust duct, which can reflect the pressure change in the first exhaust duct; one is connected by means of a pressure measuring hole near the center of the hollow cylinder, which can reflect the pressure change in the hollow cylinder; one is arranged on the hollow cylinder, measuring the pressure change of the second exhaust duct by a pressure measuring hole. In case of leakage of the wheels, three pressure sensors will detect the increase of pressure. At this point, we need to increase the height of the second exhaust duct, so that the viscous friction decreases when the air flows through the second exhaust duct, thereby reducing the pressure distribution in the second exhaust duct (that is, the A-B and E-F surface). In addition, because the exhaust resistance of the second exhaust duct decreases, more air flows through the second exhaust duct, thereby reducing the airflow through the first exhaust duct, therefore reducing the pressure in the first exhaust duct, thereby reducing the pressure distribution of the C-D surface. To sum up, we can increase the height of the second exhaust duct until the detected values of three pressure sensors drops to the lowest value, ensuring that the pressure which the vehicle bears is at or near the maximum value.

Embodiment 4

Figure 6:
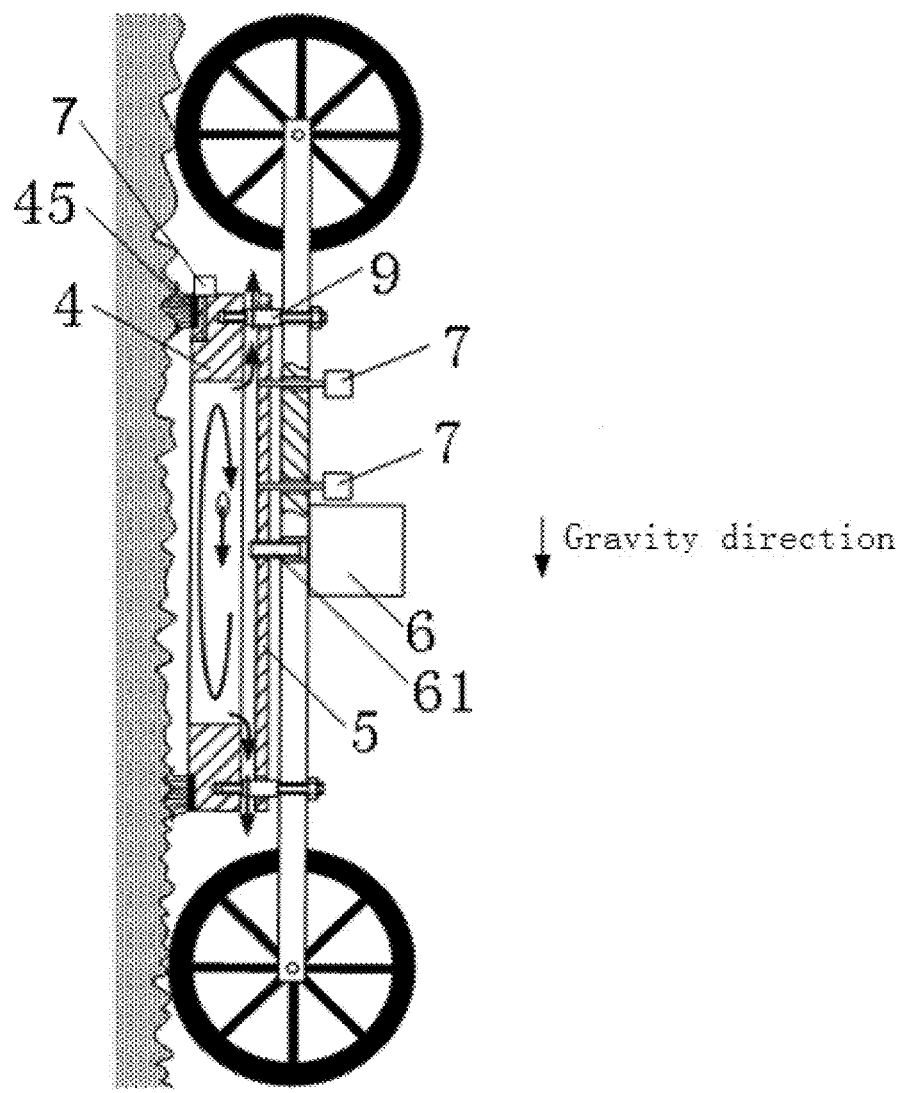
FIG. 6 represents a schematic diagram of the embodiment 4 of the invention (on the basis of the embodiment 2, a soft pad is provided)

According to FIG. 6, on the basis of the above embodiment 2, the outer edge of the lower end face of the hollow cylinder is provided with a soft pad 45.

In this embodiment, the lower end face of the hollow cylinder facing the wall is provided with a soft pad. The soft pad is made of a soft material, with one end of the soft material fixed on the hollow cylinder, and the other end in contact with the wall. For example, the soft pad may be a bristle strip, with one end of the bristle strip stuck on the hollow cylinder, and the other end in contact with the wall. Even if the wall is not flat, the bristle strip can stay close to the wall, so that no gap exists between the wall and the bristle strip. On the one hand, because the bristle strip is soft, it will not affect the movement of the vehicle on the wall. On the other hand, a very large flow resistance is formed between the bristle strip and the hollow cylinder. Although the bristle strip itself also has gaps, it is enough to block the air inside the hollow cylinder from being exhausted from the second exhaust duct. The reason is that when the height of the exhaust duct is set to the appropriate value, the pressure is very close to the atmospheric pressure, i.e., there is no great difference between the pressure inside the exhaust duct and the external environment pressure. Thus, the flow resistance caused by the bristle strip is enough to block the air inside the hollow cylinder from being exhausted from the second exhaust duct, so almost all the air will be exhausted from the flat first exhaust duct.

Figure 7:
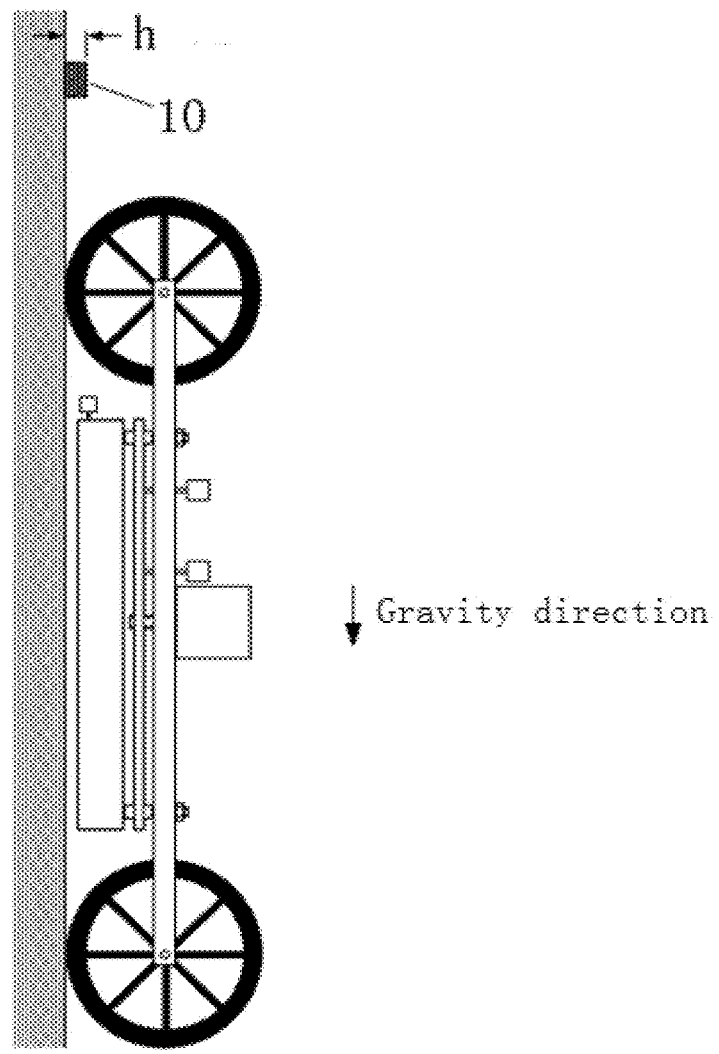
FIG. 7 represents a schematic diagram when there are obstacles ahead of the robot vehicle of the invention.

When the wall which the robot vehicle climbs is not flat, if there is no said soft pad, air will be exhausted from the second exhaust duct between the hollow cylinder and the wall, and the uneven wall will make the flow of air in the exhaust duct disordered. The disorder flow can produce a high pressure distribution in the second exhaust duct and the high pressure distribution may be asymmetric in the circumferential direction. This high pressure distribution in the second exhaust duct not only exerts a repulsive force on the hollow cylinder, but also makes the pressure distribution in the hollow cylinder moving towards the direction of the high pressure. These will weaken the pressure which the vehicle bears and is not conducive for the vehicle to be attached to the wall. After setting up a soft pad (such as a bristle strip), the soft pad is always attached to the wall, so it can form a very large flow resistance between the hollow cylinder and the wall; the flow resistance can prevent the air from being exhausted through the second exhaust duct. A soft pad can bring the following benefits:

(1) because of the blockage of the airflow in the second exhaust duct, the disorder flow of the second exhaust duct is eliminated, and the influence of the uneven wall on the rotation of the hollow cylinder is inhibited maximally;

(2) the space between the chassis of a robot vehicle (i.e., the lower end face of the adsorption mechanism) and the wall should be as great as possible. The greater the space, the bigger barrier the robot vehicle will be able to cross. For example, as shown in FIG. 7, there is a block barrier in front of the robot vehicle. If the space between the hollow cylinder and the wall is less than the height of the barrier, it is obvious that the robot vehicle is unable to cross the barrier. The soft pad blocks the airflow in the second exhaust duct, then the height of the second exhaust duct can be increased appropriately, which can increase the space between the lower end face of the hollow cylinder and the wall, so as to improve obstacle surmounting capability of the robot vehicle.

The soft pad blocks the air inside the hollow cylinder from being exhausted from the second exhaust duct, so almost all the air will be exhausted from the flat first exhaust port. We need to adjust the height of the first exhaust duct to ensure that the pressure of the C-D surface is at the lowest level, and thus ensure that the pressure which the vehicle bears is at or near the maximum value.

Embodiment 5

Figure 8:
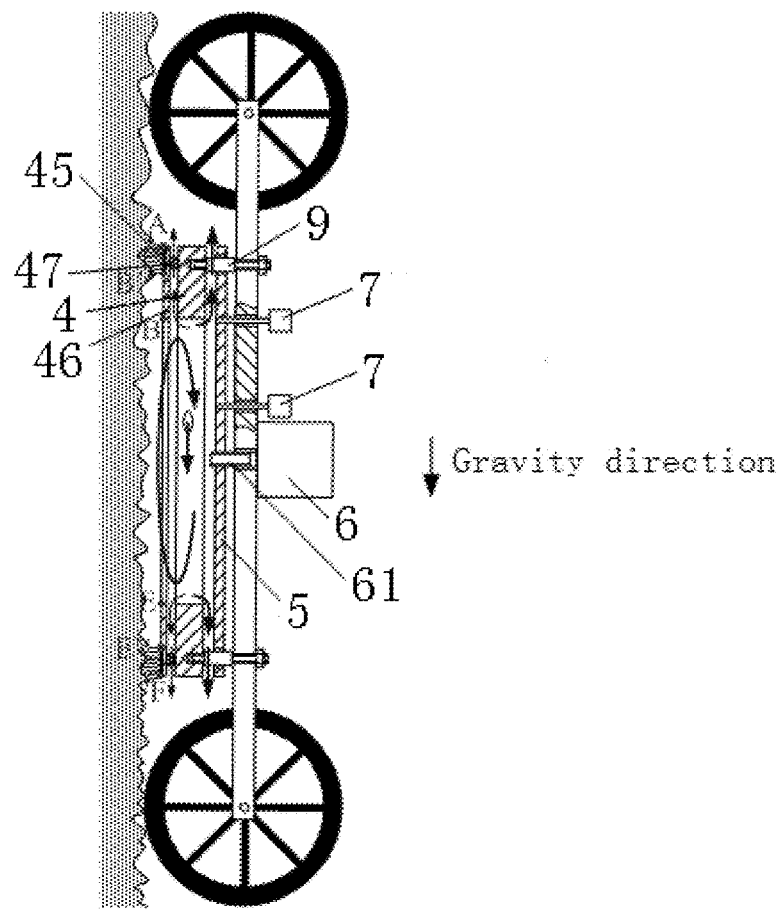
FIG. 8 represents a schematic diagram of the embodiment 5 of the invention.
Figure 9:
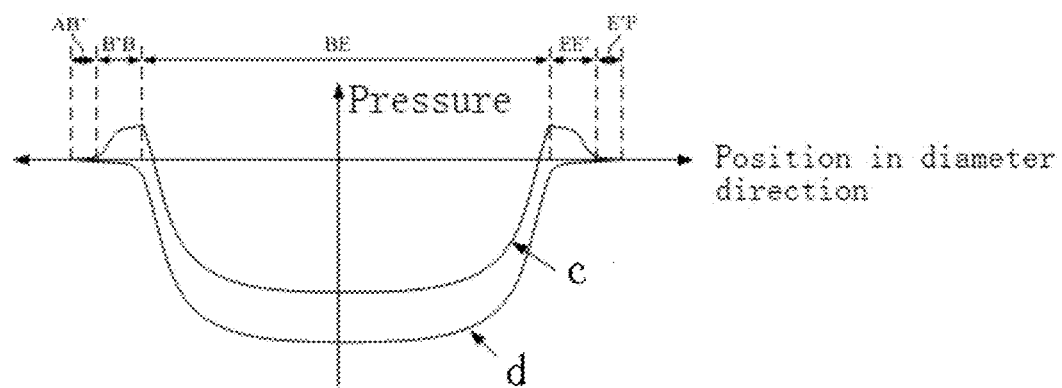
FIG. 9 represents a comparison view of pressure distribution between a embodiment of not setting the third exhaust duct and a embodiment of setting the third exhaust duct.

According to FIGS. 8 and 9, on the basis of the above embodiment 4, the lower part of the hollow cylinder 4 is provided with an annular baffle 46, the upper end surface of the annular baffle 46 is fixedly connected with the outer edge of the lower end face of the hollow cylinder 4 by means of the second blocks 47; the second blocks 47 cover part of the area of the annular baffle 46. The space between the second blocks 47 forms a third exhaust duct between the outer edge of the lower end face of the hollow cylinder and the annular baffle. The third exhaust duct connects the interior of the hollow cylinder and the outer peripheral environment. The lower end face of the annular baffle is provided with a soft pad, wherein the soft pad is a bristle strip.

In this embodiment, the purpose of setting the third exhaust duct is to reduce the pressure on the A-B surface and the E-F surface (the B-B' and E-E' surface as shown in figure) where the soft pad does not cover. Here is a detailed explanation.

In order to achieve a good sealing effect, the soft pad is usually arranged in the periphery of the lower end face of the annular baffle. A gap will exist between the annular baffle and the wall where the soft pad doesn't cover (the BB' and EE' surface as shown in figures). This gap will lead to the formation of a high pressure distribution for the reason that the air will be thrown to the outer periphery by the centrifugal force of the rotating flow; if there is no exhaust duct in the periphery, high pressure will be formed. According to this theory and experimental verification, after the soft pad is used to block the flow of air in the second exhaust duct between the lower end face of the annular baffle and the wall, the pressure distribution of the B-B' and E-E' surface is moved towards the direction of the high pressure, as shown in FIG. 9, and a weakly high pressure distribution is formed in the gap, which acts as a repulsive force on the annular baffle, so as to weaken the pressure of the robot vehicle. After adding the third exhaust duct on the hollow cylinder it connects the inner and outer peripheral environment of the hollow cylinder, and the third exhaust duct is close to the A-B and E-F surface. The dense air around the entrance of the duct can be exhausted from the third exhaust duct, so as to reduce the pressure near the entrance of the duct. Also, because the duct is close to the A-B and E-F surface, it can reduce the pressure of the B-B' and E-E' surface. In FIG. 9, "c" is the pressure distribution without setting the third exhaust duct and "d" is pressure distribution when setting the third exhaust duct. The results show that the pressure distribution after setting the third exhaust duct integrally moves towards the direction of low pressure, and a weakly low pressure also forms on the B-B' and E-E' surface. These factors can increase the pressure on the robot vehicle.

Further, according to the pressure of each surface, the height of the third exhaust duct is designed to be automatically adjusted to ensure that the pressure which the vehicle bears is at or near the maximum value.

Figure 10A:
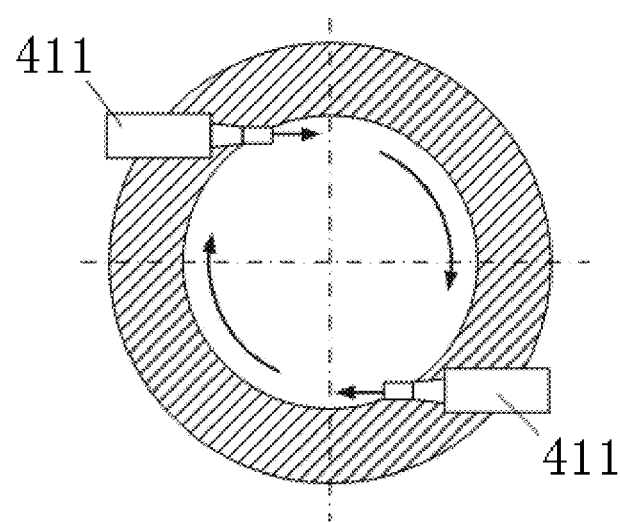
FIG. 10a represents a connection schematic diagram of the tangential nozzle and a turbojet of the invention.
Figure 10B:
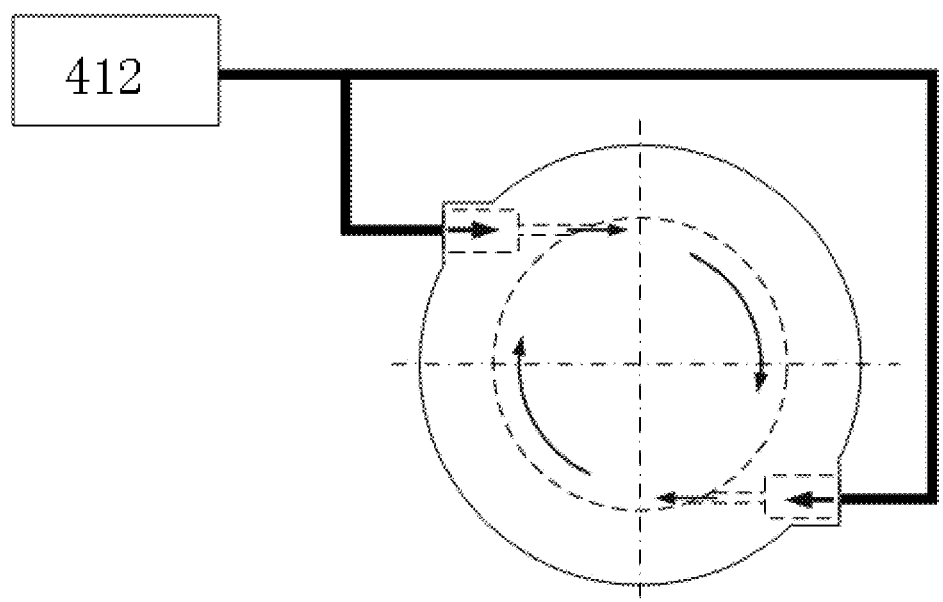
FIG. 10b represents a connection schematic diagram of the tangential nozzle and a fuel engine of the invention.

According to FIGS. 10*a* and 10*b*, in embodiments 1-5, a high-speed airflow ejected from tangential nozzles is required to form a high-speed rotating flow in the hollow cylinder. Usually, each of the nozzles is connected with a high pressure gas source through a gas pipe to achieve the air supply. An air compressor is usually used as the high pressure air source. Because a compressor is very heavy, we can't put a compressor on the climbing robot vehicle, and we can only separate the compressor and the climbing robot vehicle. This will bring the following problems: (1) the gas pipe between the compressor and the robot vehicle will limit the moving range of the robot vehicle; (2) the robot vehicle can work only when there is a compressor, which limits the application range of the robot vehicle; (3) when the compressor supplies airflow through the gas pipe, the gas pipe will produce a pressure loss, and the longer is the gas pipe, the greater is the pressure loss, which will result in shortage of the pressure at the exit of the gas pipe (i.e., the inlet of the nozzle).

In order to solve the above problems, we use a fuel engine to solve the problem of high pressure gas supply. The fuel engine produces a high pressure air flow by means of the explosion of fuel (e.g., gasoline, diesel, etc.). A small turbojet engine 411 is used to replace the high pressure gas source in FIG. 10*a*, which is installed at the tangent position of the hollow cylinder. The gas generated during the combustion of fuel is injected into the hollow cylinder by a small turbine engine, thereby forming a rotating flow in the hollow cylinder. A fuel engine 412 is used to replace the high pressure gas source in FIG. 10*b*, wherein the nozzle is connected with the fuel engine by the gas pipe. The fuel engine, which is connected with the nozzle by the gas pipe, generates a high pressure airflow through combustion and explosion. This technical scheme can well solve the above-mentioned problems: (1) a fuel engine has a small volume and a light weight, which can be directly installed on the vehicle, therefore, the vehicle does not need to be connected with external devices and the moving range will not be limited; (2) after filled with fuel, the robot vehicle can work in any place, widening its application range; (3) since the fuel engine is directly installed on the vehicle, the gas pipe between the engine and the nozzle is very short, so the pressure loss in the gas pipe can almost be neglected, thus the inlet pressure of the nozzle can be guaranteed.

The embodiments described in this specification are cases of work under atmospheric conditions. The climbing robot vehicle can also work in a liquid environment, for example, the climbing robot vehicle of the invention can work in deep sea. When working in the liquid environment, we can use a pump to supply high pressure water flow to the tangential nozzle, and the water flows from the nozzle and rotates in the hollow cylinder. The principle of generating the pressure is the same as that of embodiments 1-5. Here, high pressure gas source and high pressure liquid source are collectively referred to as high pressure fluid source.

In order to increase the pressure, the number of the adsorption mechanism(s) is not limited to one, but also may be plural.

The contents which the embodiments of this specification represent are merely a list of the realization forms of the invention. The protecting scope of the invention should not be seen as being limited to specific forms which the embodiments represent, and the protecting scope of the invention are also involved in equivalent technical means which those skilled in the art can conceive according to the concepts of the invention.

What is claimed is:

1. A climbing robot vehicle capable of climbing a wall, comprising:
    a vehicle; and
    a sucking mechanism in connection with the vehicle, the sucking mechanism further comprising a hollow cylinder body and a cover plate connected to the hollow cylinder body via a plurality of first blocks,
    wherein the inner wall of the hollow cylinder is provided with tangential nozzles,
    wherein a first exhaust duct is formed by a space between the plurality of first blocks,
    wherein a second exhaust duct is formed between the hollow cylinder body and the wall, and
    wherein each of the first exhaust duct and the second exhaust duct connects the interior of the hollow cylinder body with the outer peripheral environment respectively.

2. The climbing robot vehicle of claim 1, wherein the height of the first exhaust duct is adjustable.

3. The climbing robot vehicle of claim 1, wherein the height of the second exhaust duct is adjustable.

4. The climbing robot vehicle of claim 1, wherein the vehicle is provided with an electric motor which is connected to the cover plate, and wherein the hollow cylinder body and the cover plate are provided with pressure measuring holes in connection with pressure sensors.

5. The climbing robot vehicle of claim 1, wherein the vehicle is connected with the hollow cylinder body by means of connecting rods.

6. The climbing robot vehicle of claim 1, wherein the vehicle is provided with guide holes and a guide column configured to slide in the guide hole.

7. The climbing robot vehicle of claim 1, wherein the hollow cylinder body is provided with a soft pad.

8. The climbing robot vehicle of claim 7, wherein the soft pad is a bristle strip.

9. The climbing robot vehicle of claim 7, wherein the lower part of the hollow cylinder body is provided with an annular baffle that is connected to the hollow cylinder body via a plurality of second blocks, wherein the space between the plurality of second blocks forms a third exhaust duct connecting the interior of the hollow cylinder body with the outer peripheral environment.

10. The climbing robot vehicle of claim 9, wherein the plurality of first blocks are equally spaced, and the plurality of second blocks are equally spaced.

11. The climbing robot vehicle according to claim 1, wherein said tangential nozzles are connected with a high pressure fluid source by a tube.

* * * * *